United States Patent [19]

Murphy et al.

[11] 4,403,207

[45] Sep. 6, 1983

[54] DURABLE TITANIA EXHAUST GAS SENSOR

[75] Inventors: Michael P. Murphy, Flint; James S. Hoffman, Grand Blanc, both of Mich.

[73] Assignee: General Motors Corporation, Detroit, Mich.

[21] Appl. No.: 314,756

[22] Filed: Oct. 26, 1981

[51] Int. Cl.$^3$ .............................................. H01L 7/00
[52] U.S. Cl. ..................................................... 338/34
[58] Field of Search ........... 338/34; 324/71 R, 715 N; 73/27 R; 422/98; 23/232 E, 254 E

[56] References Cited

U.S. PATENT DOCUMENTS

| 4,012,709 | 3/1977 | Logothetis et al. | 338/34 |
| 4,066,413 | 1/1978 | Segawa et al. | 23/254 E |
| 4,249,156 | 2/1981 | Micheli | 338/34 |

*Primary Examiner*—C. L. Albritton
*Attorney, Agent, or Firm*—Douglas D. Fekete

[57] ABSTRACT

A durable automotive exhaust gas oxygen sensor comprises a ceramic sleeve defining a bore and a titania pellet positioned in the bore against a shoulder thereof. Terminal rods and at least one spacer within the bore securely hold the pellet against the shoulder. The rods, spacer and sleeve are bonded together into a unified assembly by a fused glass seal within the bore that is spaced apart from the pellet.

3 Claims, 5 Drawing Figures

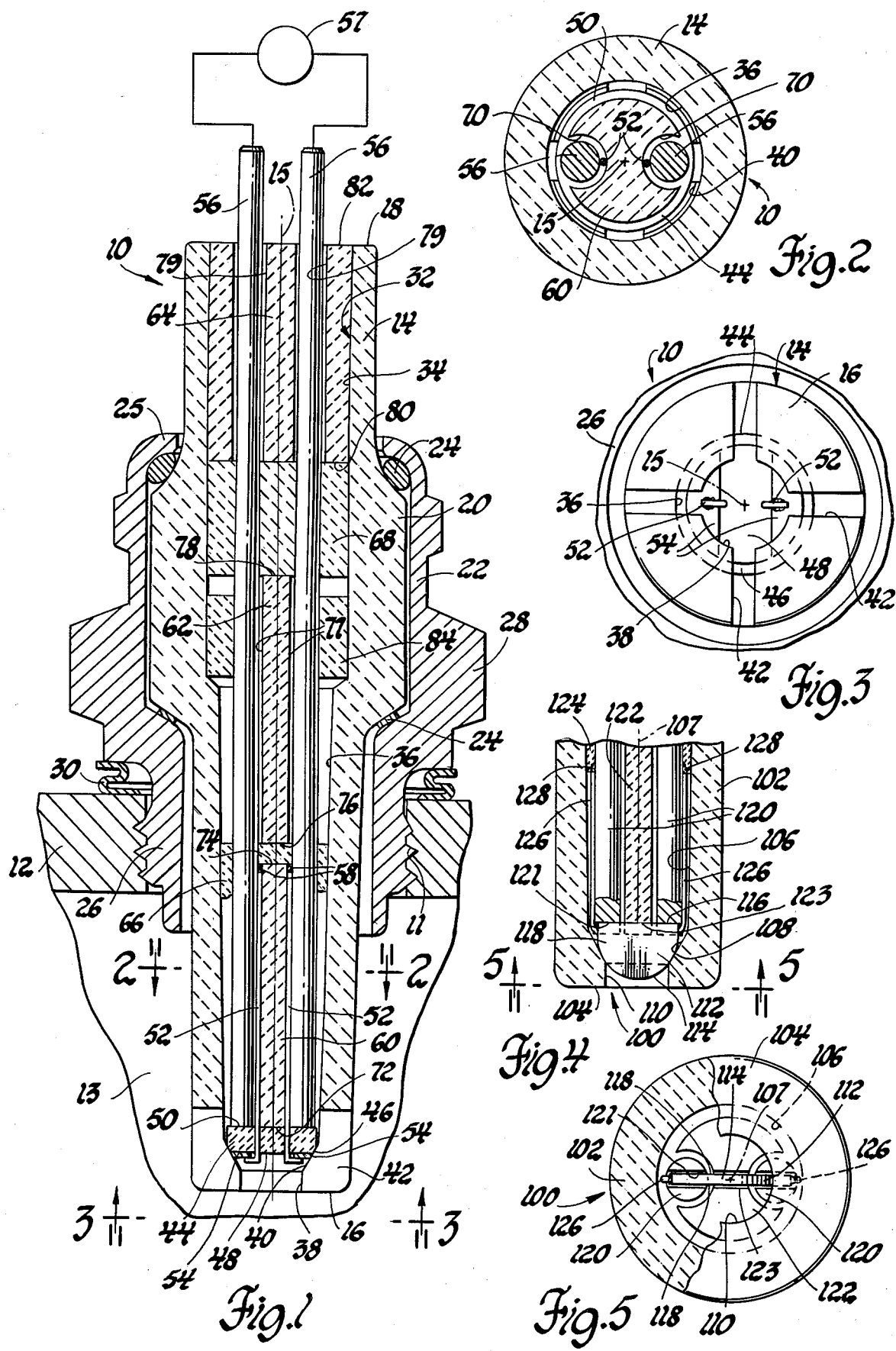

DURABLE TITANIA EXHAUST GAS SENSOR

BACKGROUND OF THE INVENTION

This invention relates to a titania resistive-type gas sensor for detecting oxygen in automotive exhaust gases. More particularly, this invention relates to an oxygen sensor wherein electrical resistance is measured through a titania pellet between embedded very thin platinum wires, which sensor is ruggedly constructed for prolonged use on board an automotive vehicle.

The electrical resistivity of titanium dioxide, more commonly called titania, is known to change in response to changes in the ambient oxygen partial pressure. Accordingly, the oxygen content of automotive exhaust gases may be monitored by exposing a titania pellet to the gases and measuring its electrical resistance. A suitable titania pellet is manufactured by compacting and sintering titania particles, as described, for example, in U.S. Pat. No. 4,249,156, issued to Micheli in 1981. In order to obtain good electrical contact with the titania, very thin platinum wires are embedded in the compact and cofired with the titania to produce an intimate bond. The platinum wires are very thin, typically on the order of 0.008 inch diameter, to prevent damage to the pellet due to differential thermal expansion, either during firing or during automotive operations. The thin wires are connected to thicker terminals, which in turn are connected to a resistance measurement circuit. However, when the pellet is incorporated into a sensor and mounted in an exhaust system on board an automobile, vibrations, thermal cycling and other conditions associated with automotive operation tend to break the very thin wires or to loosen the wire-pellet connections, particularly where the pellet is suspended in the gas stream solely by the wires.

Therefore, it is an object of this invention to provide an improved resistive-type exhaust gas oxygen sensor having a durable construction for better withstanding automotive operating conditions to extend the useful life of the sensor on board a vehicle. The sensor comprises a titania pellet immovably wedged in position therein. Thus, the pellet is not supported by and does not stress any attached thin wires required for electrical connections. In addition, this invention provides a sensor that can be readily assembled so as to wedge the pellet in position.

SUMMARY OF THE INVENTION

In a preferred embodiment, an oxygen sensor of this invention comprises an electrically insulative ceramic tubular body defining an elongated cavity divided longitudinally into a terminal-receiving portion and an exhaust gas opening by a beveled shoulder that faces the terminal-receiving portion. An oxygen-sensitive titania pellet sits upon the shoulder and is exposed to exhaust gases through the opening. Electrically conductive terminal rods extend through the said cavity portion and press the pellet securely against the shoulder. Because mere contact of the rods to the pellet is not sufficient for sensitive resistive measurements, good electrical connections are provided by thin platinum wires cofired in the pellet and welded to the rods. A ceramic insulative spacer member that separates and electrically isolates the terminal rods within the cavity also presses the pellet against the shoulder. Fused glass seals within the cavity spaced apart from the pellet bond the body, rods and spacer together to form a unified, durable construction that locks the pellet in position. This unified construction reduces breakage of the wires under automotive operating conditions and thereby extends the useful life of the sensor.

DESCRIPTION OF THE DRAWINGS

FIG. 1 is a longitudinal cross-sectional view of a durable oxygen sensor of this invention;

FIG. 2 is a cross-sectional view of the sensor in FIG. 1 taken along the lines 2—2 and looking in the direction of the arrows;

FIG. 3 is an end plan view of the sensor in FIG. 1 taken along the lines 3—3 and looking in the direction of the arrows;

FIG. 4 is a longitudinal cross-sectional view of an exhaust end portion of an alternate sensor embodying this invention and showing an alternate pellet arrangement; and FIG. 5 is an end plan view, partially cut away, of the sensor in FIG. 4 taken along the lines 5—5 and looking in the direction of the arrows.

DETAILED DESCRIPTION OF THE INVENTION

Referring to FIGS. 1 through 3, a preferred oxygen sensor 10 is intended to be mounted through a threaded opening 11 in an automotive exhaust manifold wall 12 for monitoring the oxygen content of exhaust gas stream 13 flowing through the manifold. Sensor 10 comprises a ceramic sleeve 14 generally cylindrical about axis 15 and formed of an electrically insulative alumina material. Inner end 16 of sleeve 14 lies in the exhaust stream 13 and outer end 18 lies outside manifold wall 12.

An enlarged portion 20 of sleeve 14 is concentrically enclosed by a metal shell 22 and securely held through malleable steel spacer rings 24 that deform to provide a tight hermetic fit while preventing damage to the ceramic when outer end 25 of shell 22 is rolled over during assembly. Axially inwardly depending from shell 22 is an outwardly threaded skirt 26 adapted to mate with threaded opening 11 in wall 12. Shell 22 also has a hexagonal nut portion 28 for engaging a wrench for torquing sensor 10 into the opening. A folded steel seating gasket 30 between shell 22 and wall 12 provides a gas-tight seal.

Sleeve 14 defines an axial bore 32 comprising a coaxial cylindrical portion 34 immediately adjacent end 18, a gently tapered portion 36 extending from portion 34 and a circular opening 38 in end 16 communicating with exhaust stream 13. The diameter of opening 38 is significantly less than the adjacent diameter of bore portion 36 and a chamfered shoulder 40 is formed therebetween. Slots 42 in end 16 promote gas flow into and out from opening 38 so that the gas composition therein is representative of the exhaust stream.

An oxygen sensitive disk-shaped pellet 44 is positioned in bore 32 near end 16 normal to axis 15 and has a chamfered edge 46 that abuts shoulder 40. Pellet 44 is formed of a titanium dioxide material whose resistivity depends upon the ambient oxygen concentration. An inner pellet face 48 faces end 16 and is exposed to exhaust gas through opening 38. The opposite outer face 50 faces end 18. Two platinum wires 52 extend axially through pellet 44 and are welded to two sputtered platinum electrodes 54 carried on inner surface 48. As best seen in FIG. 3, electrodes 54 are spaced apart by exposed titania and one wire 52 is connected to each electrode. It has been found that sputtering electrodes 54 and welding wires 52 thereto improves electrical contact between the titania material and the wires.

Two terminal rods 56 extend axially through bore 32 to pellet face 50 and urge pellet 44 against shoulder 40. Rods 56 are formed of a relatively inexpensive, electrically conductive iron alloy and are substantially thicker than wires 52. For example, rods 56 are about 0.063 inch in diameter, whereas wires 52 are about 0.008 inch in diameter to allow the wires to be cofired in pellet 44 and subjected to extreme thermal cycling without breakage. The rods and platinum wires are connected by welds 58. Because platinum is expensive, it is desired to minimize the distance between pellet 44 and welds 58, while providing a sufficient length for convenient welding and assembly. Rods 56 protrude above sleeve end 18 to permit electrical connection to a suitable ohmmeter 57 for measuring the electrical resistance between rods 56 across pellet 44.

Rods 56 are physically separated and electrically isolated within bore 32 by electrically insulative ceramic spacer members 60, 62 and 64 and fused glass seals 66 and 68 that bond the spacers, terminal rods and sleeve together into a durable assembly. As seen in FIG. 2, spacer 60 is shaped generally cylindrical with its longitudinal axis colinear with axis 15 and has axial grooves 70 for receiving wires 52 and terminal rods 56. Spacer 60 has an inner end 72 that abuts pellet face 50 and cooperates with rods 56 in pressing pellet 44 against shoulder 40. The outer end 74 is adjacent wire-rod welds 58 and glass seal 66. Seal 66 is sandwiched between end 74 of spacer 60 and inner end 76 of spacer 62. Spacer 62 is similarly cylindrically shaped to spacer 60 with terminal rod-receiving grooves 77 and is coaxial about axis 15. Seal 66 covers wire-rod welds 58 to reinforce and protect them against corrosion by exhaust gases. Seal 68 lies between the outer end 78 of spacer 62 and inner end 80 of coaxial cylindrical spacer 64. Rods 56 pass through round enclosed axial channels 79 in spacer 64. The outer end 82 of spacer 64 is flush with sleeve end 18. An annular fused glass seal 84 about rods 56 and spacer 62 within bore portion 34 helps bond the assembled elements into a solid construction.

Sensor 10 is manufactured as follows: Pellet 44 is formed by compacting and sintering titania powder. Platinum wires 52 are embedded in and cofired with pellet 44. Platinum electrodes 54 are sputtered onto pellet face 48. Wires 52 are bent and welded to the electrodes. The wires are then welded at 58 to terminal rods 56. Spacers 60, 62 and 64 and porous glass preforms for forming seals 66, 68 and 84 are then arranged with the pellet and rods to form a subassembly. This subassembly is inserted into bore 32 of sleeve 14 through end 18, whereupon pellet 44 is securely pinned against shoulder 40 by rods 56. The preforms, particularly for forming seals 66 and 68, have longitudinal dimensions along axis 15 greater than the seal dimensions, so that, when the subassembly is inserted in the sleeve, spacer 64 protrudes above sleeve end 18. While maintaining pressure on rods 56 to hold pellet 44 tightly against shoulder 40, the assembly is then heated to fuse the glass, whereupon pressure is applied axially to the outer end 82 of spacer 64 to squeeze the spacers together until end 82 is flush with sleeve end 18, densifying seals 66 and 68 in the process. As seen in FIG. 1, the gap between rods 56 or spacer 60 and tapered bore portion 36 progressively narrows as it approaches pellet 44. The gap becomes sufficiently narrow so that the viscous fused glass cannot flow through it when the spacers are squeezed. In this matter, the fused glass for seal 66 is contained near end 74 of spacer 60 and is prevented from contacting and damaging the pellet. Upon cooling, the fused glass bonds sleeve 14, rods 56 and spacers 60, 62 and 64 into a unified construction securely wedging pellet 44 in position.

When sensor 10 is mounted in manifold 12, pellet 44 is exposed to the exhaust stream 13 through opening 38. The resistance across pellet 44 is readily measured by connecting ohmmeter 57 to rods 56, which are in turn connected to the pellet through platinum wires 52. Because the pellet is wedged between shoulder 42 and rods 56 and spacer 60, the wires 52 do not support the pellet weight. This reduces breakage of wires 52 and extends the useful lifetime of sensor 10.

FIGS. 4 and 5 depict a portion of a sensor 100 showing an alternate pellet arrangement embodying this invention. Sensor 100 comprises a ceramic sleeve 102 having an end 104 adapted to lie in an exhaust gas stream. Sleeve 102 defines a bore 106 generally cylindrical about axis 107 and comprising a chamfered shoulder 108 and a circular opening 110 in end 104 for exhaust gas communication. A "D"-shaped disk-like titania pellet 112 is positioned in bore 106 such that semicircular edge 114 abuts shoulder 108, flat edge 116 is normal to axis 107 and faces 118 are parallel to the axis.

Two terminal rods 120 extend axially through bore 106 and press against flat edge 116 of pellet 112, thereby pressing round edge 114 against shoulder 108 to wedge pellet 112 in position. End slots 121 in rods 120 receive edge 116 for holding pellet 112 edgewise or upright in bore 106. An insulative ceramic spacer 122, similar in cross-section to spacer 60 in FIG. 1, is located in bore 106 between rods 120 to electrically isolate the rods. Spacer 122 comprises an end slot 123 that receives pellet edge 116. The spacer thus abuts pellet 112 and cooperates with rods 120 to urge it against shoulder 108. Rods 120, spacer 122 and sleeve 102 are bonded together by a fused glass seal 124 to form a unified durable construction holding the pellet securely in position.

Two very thin platinum wires 126 are diametrically embedded in edge 114 of pellet 112, extend axially adjacent the surface of bore 106 and are welded to terminal rods 120 at welds 128, thereby electrically connecting rods 120 and pellet 112 for the purpose of measuring the resistance of the titania. The remainder of sensor 100 is substantially similar to the sensor in FIG. 1. Thus, when suitably mounted in an automotive exhaust system, titania pellet 112 is exposed to exhaust gas through opening 110. The resistance of the titania, and thus the oxygen content of the exhaust gas, is measured by connecting a suitable ohmmeter to rods 120, which are in turn connected to the pellet by thin embedded wires 126. Because the pellet is pinned against shoulder 108 by rods 120 and spacer 122, thin wires 126 do not carry the weight of the pellet, which reduces the tendency of the wires to break during gas sensing under automotive operating conditions.

Although this invention has been described in terms of certain embodiments thereof, it is not intended to be limited to the above description, but rather only to the extent set forth in the claims that follow.

The embodiments of the invention in which an exclusive property or privilege is claimed are defined as follows:

1. A durable oxygen gas sensor having a unified construction and comprising:
- a ceramic tubular body defining an elongated bore comprising an end opening for communicating with a gas for detecting oxygen therein and a terminal-receiving longitudinal portion remote from the gas opening, said body forming a beveled shoulder about the bore facing the terminal-receiving portion and sized and shaped to support a body in said portion against displacement toward said gas opening,
- an oxygen-sensitive titania pellet within the bore supported by the shoulder and exposed to gas through the gas opening,
- at least two terminal rods suitable for electrically connecting the pellet to an external circuit for measuring an electrical resistance of the pellet, said terminal rods extending through the terminal-receiving bore portion and each rod having an end abutting the pellet and pressing the pellet in the direction of the gas opening,
- a ceramic spacer member electrically isolating the terminal rods within the terminal-receiving bore portion, said spacer member abutting and pressing the pellet in the direction of the gas opening, and
- means for bonding the terminal rods, spacer member and body together at a location within the bore spaced apart from the pellet, whereby the pellet is securely held against the shoulder by the terminal rods and the spacer member.

2. A durable automotive exhaust gas oxygen sensor comprising:
- a ceramic sleeve adapted to be mounted through a wall of an automotive exhaust system such that a first end lies in an exhaust gas stream and a second end lies outside the exhaust system, said sleeve defining an axial bore extending between said ends and comprising a gas opening in the first end for exhaust gas communication, a relatively wider terminal-receiving portion opening at the second end and a chamfered shoulder therebetween facing the terminal-receiving portion,
- an oxygen-sensitive titania pellet within the terminal-receiving bore portion, said pellet having a generally disk-like shape and a chamfered edge abutting the chamfered shoulder, said pellet having a first major surface communicating with the gas opening and a second opposite major surface facing the terminal-receiving bore portion such that pressure applied to said second surface holds the pellet against the shoulder,
- two axial spaced terminal rods extending from the second end through the terminal-receiving bore portion and electrically connected to the pellet for permitting a measurement of a resistance of the titania, each rod having an inner end abutting the pellet second surface so as to urge the pellet against the shoulder,
- a ceramic spacer member within the terminal-receiving bore portion spacing apart the terminal rods, said spacer abutting the pellet second surface so as to urge the pellet against the shoulder, and
- fused glass seal means spaced apart from the pellet and bonding the terminal rods, the spacer member, and the sleeve together to form a unified assembly wherein the pellet is securely wedged against said shoulder by said terminal rods and said spacer member.

3. A durable oxygen gas sensor comprising:
- an electrically insulative body defining a cavity having an opening for communicating with an external gas for detecting oxygen therein and an elongated portion apart from the opening, said body forming shouldering means facing the cavity for supporting a body within the elongated portion against displacement toward the gas opening,
- a pellet formed of a material whose electrical resistance is responsive to changes in oxygen content of gas in contact therewith, said pellet being supported within the cavity by the shouldering means and exposed to gas through said gas opening,
- terminal rods extending through the cavity elongated portion and pressing against the pellet,
- an electrically insulative spacer member within the cavity elongated portion between the terminal rods and pressing against the pellet, and
- means for bonding the terminal rods, spacer member and body together at a location remote from the pellet, whereby the terminal rods and the spacer member cooperate to securely hold the pellet against the shouldering means.

* * * * *